(12) United States Patent
Baynham et al.

(10) Patent No.: US 8,348,982 B2
(45) Date of Patent: Jan. 8, 2013

(54) BONE FIXATION PLATE

(75) Inventors: Matthew G. Baynham, Jupiter, FL (US); G. Clay Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 680 days.

(21) Appl. No.: 12/352,265

(22) Filed: Jan. 12, 2009

(65) Prior Publication Data
US 2009/0171396 A1 Jul. 2, 2009

Related U.S. Application Data

(63) Continuation-in-part of application No. 10/419,686, filed on Apr. 21, 2003, now Pat. No. 7,481,829.

(51) Int. Cl.
*A61B 17/80* (2006.01)
(52) U.S. Cl. ...................................... 606/294
(58) Field of Classification Search .......... 606/283, 606/286, 288, 289, 295, 296; 411/16–18
See application file for complete search history.

(56) References Cited

U.S. PATENT DOCUMENTS

| | | | |
|---|---|---|---|
| 3,316,795 A * | 5/1967 | Tann | ................. 411/17 |
| 4,013,071 A | 3/1977 | Rosenberg | |
| 4,611,581 A | 9/1986 | Steffee | |
| 4,716,893 A | 1/1988 | Fischer et al. | |
| 5,180,381 A | 1/1993 | Aust et al. | |
| 5,261,911 A | 11/1993 | Carl | |
| 5,569,251 A | 10/1996 | Baker et al. | |
| 5,578,034 A | 11/1996 | Estes | |
| 5,584,832 A | 12/1996 | Schlapfer | |
| 5,603,713 A | 2/1997 | Aust et al. | |
| 5,607,426 A | 3/1997 | Ralph et al. | |
| 5,624,441 A | 4/1997 | Sherman et al. | |
| 5,643,260 A | 7/1997 | Doherty | |
| 5,688,273 A | 11/1997 | Errico et al. | |
| 5,713,900 A | 2/1998 | Benzel et al. | |
| 5,752,957 A | 5/1998 | Ralph et al. | |
| 5,800,433 A | 9/1998 | Benzel et al. | |
| 5,810,818 A | 9/1998 | Errico et al. | |
| 5,843,082 A | 12/1998 | Yuan et al. | |
| 5,885,286 A | 3/1999 | Sherman et al. | |
| 5,951,558 A | 9/1999 | Fiz | |
| 6,045,552 A | 4/2000 | Zucherman et al. | |
| 6,139,550 A | 10/2000 | Michelson | |
| 6,193,720 B1 | 2/2001 | Yuan et al. | |

(Continued)

FOREIGN PATENT DOCUMENTS
EP 0613664 9/1994

*Primary Examiner* — Anu Ramana
(74) *Attorney, Agent, or Firm* — McHale & Slavin, P.A.

(57) ABSTRACT

A bone plate for use in anterior lumbar spinal fixation has interlocking components to prevent dislodgement of the plate due to anatomical forces. The exposed surface of the plate is smooth to prevent trauma to internal body tissue. The plate spans the intervertebral space with each end attached to an adjacent vertebrae by locking screws threadably engaged with tubular bone anchors. The bone anchors include helical members are threaded through the bone plate and inserted into holes within the bone. The plate has a countersunk cavity including portions overlapping the locking screws. A locking cap fits in the cavity to secure the other end of the locking screws from backing-out of the plate. The locking cap includes at least two chamfered portions that cooperate with mating recesses in the countersunk cavity of the bone plate.

25 Claims, 13 Drawing Sheets

U.S. PATENT DOCUMENTS

| | | |
|---|---|---|
| 6,224,602 B1 | 5/2001 | Hayes |
| 6,231,610 B1 | 5/2001 | Geisler |
| 6,235,034 B1 | 5/2001 | Bray |
| 6,241,731 B1 | 6/2001 | Fiz |
| 6,306,139 B1 | 10/2001 | Fuentes |
| 6,331,179 B1 | 12/2001 | Freid |
| 6,342,055 B1 | 1/2002 | Eisermann et al. |
| 6,383,186 B1 | 5/2002 | Michelson |
| 6,413,259 B1 | 7/2002 | Lyons et al. |
| 6,436,142 B1 | 8/2002 | Paes et al. |
| 6,454,769 B2 | 9/2002 | Wagner et al. |
| 6,454,771 B1 | 9/2002 | Michelson |
| 6,458,133 B1 | 10/2002 | Lin |
| 6,613,053 B1 | 9/2003 | Collins et al. |
| 7,481,829 B2 | 1/2009 | Baynham et al. |
| 2002/0151899 A1 | 10/2002 | Bailey et al. |
| 2002/0188296 A1 | 12/2002 | Michelson |

* cited by examiner

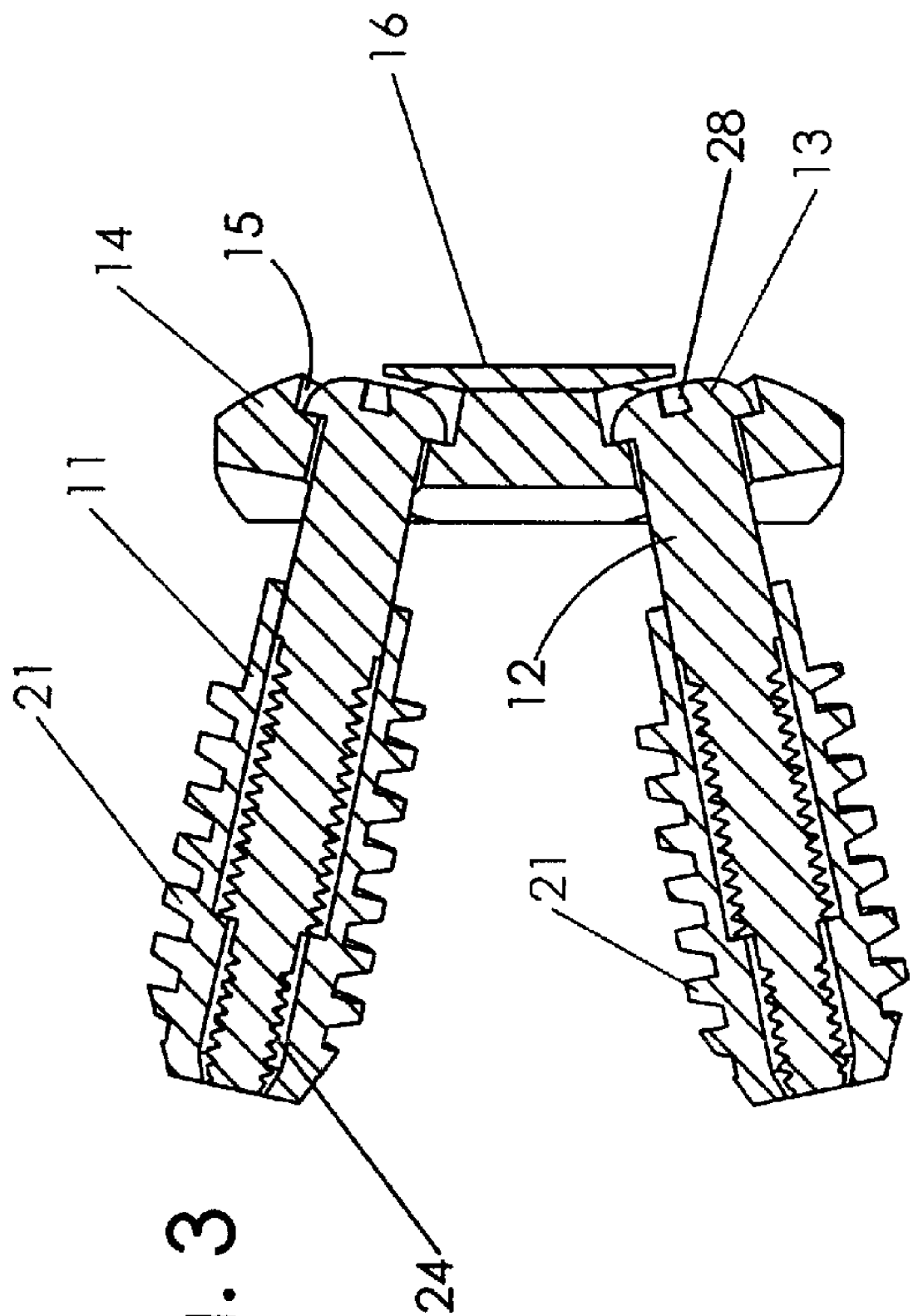

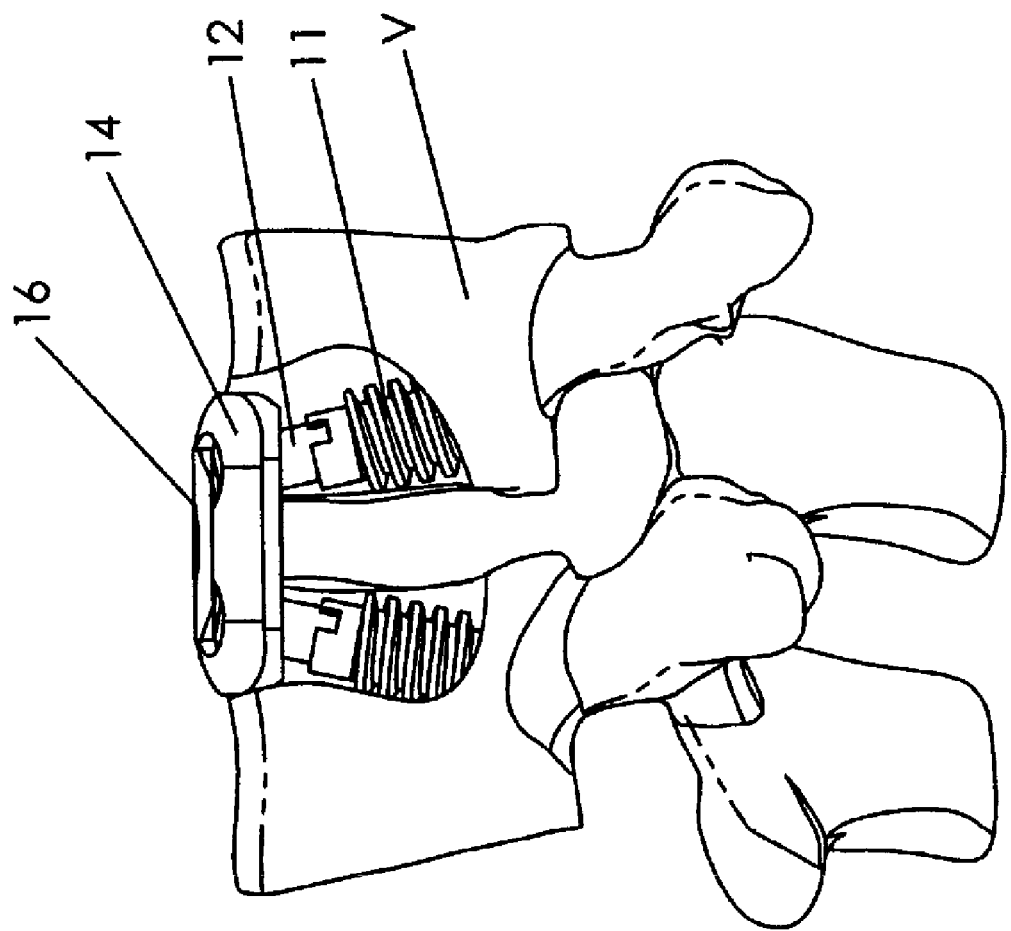

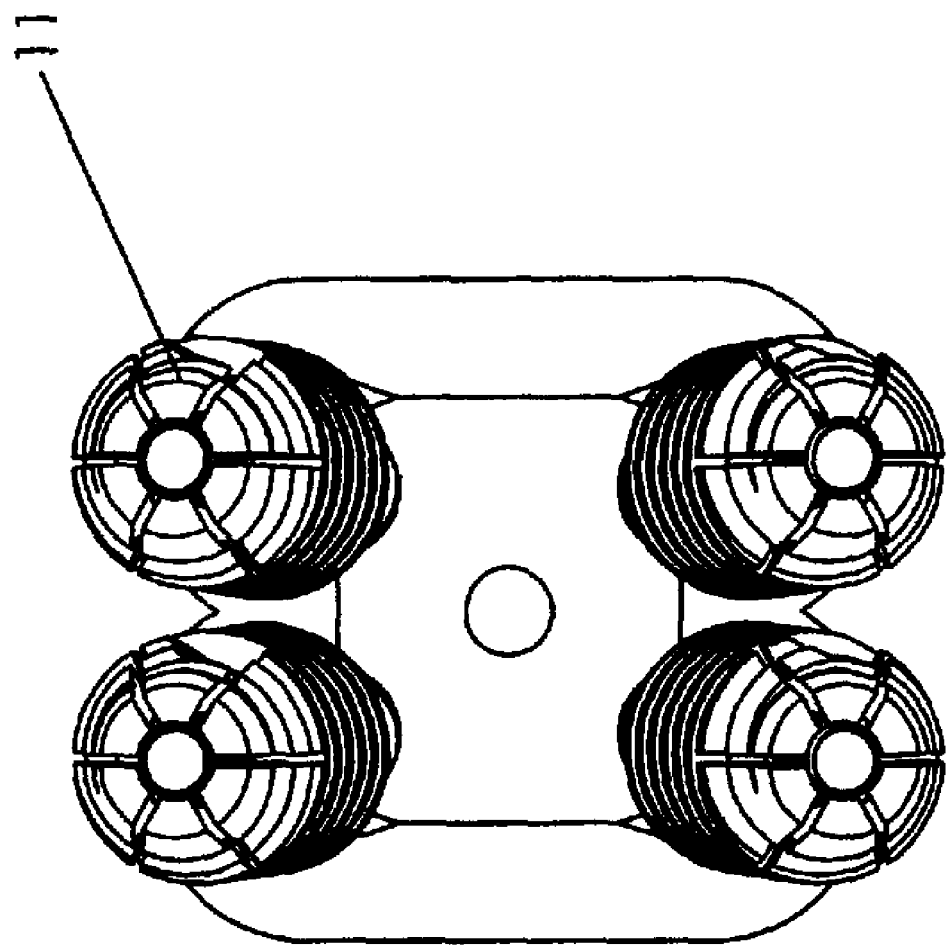

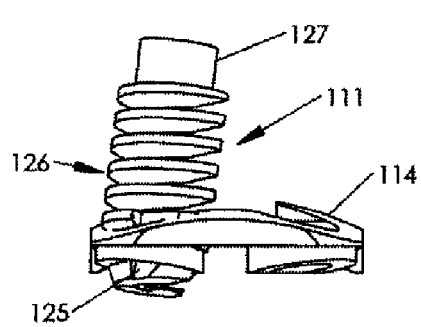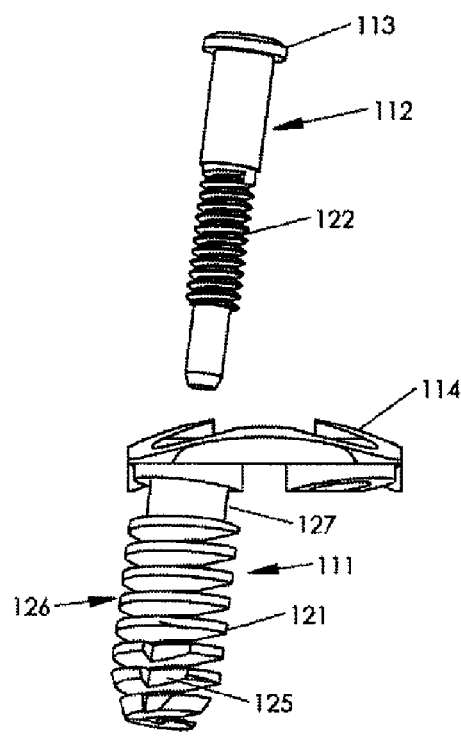
Figure 8A
Figure 8B

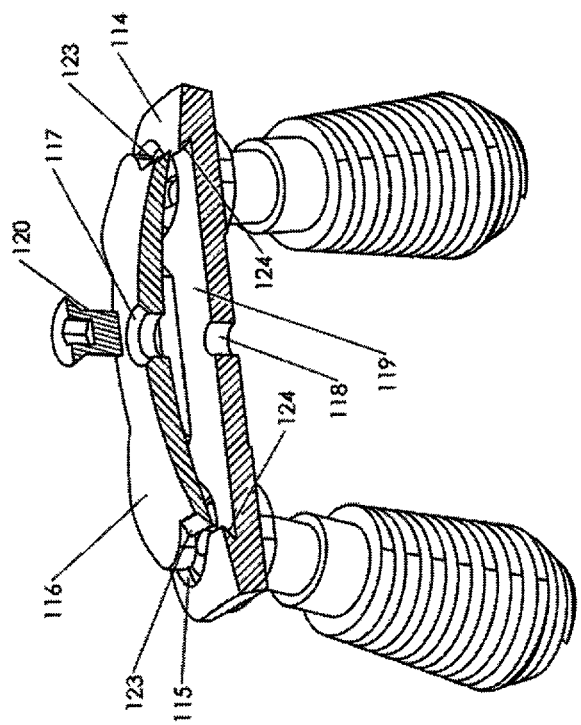
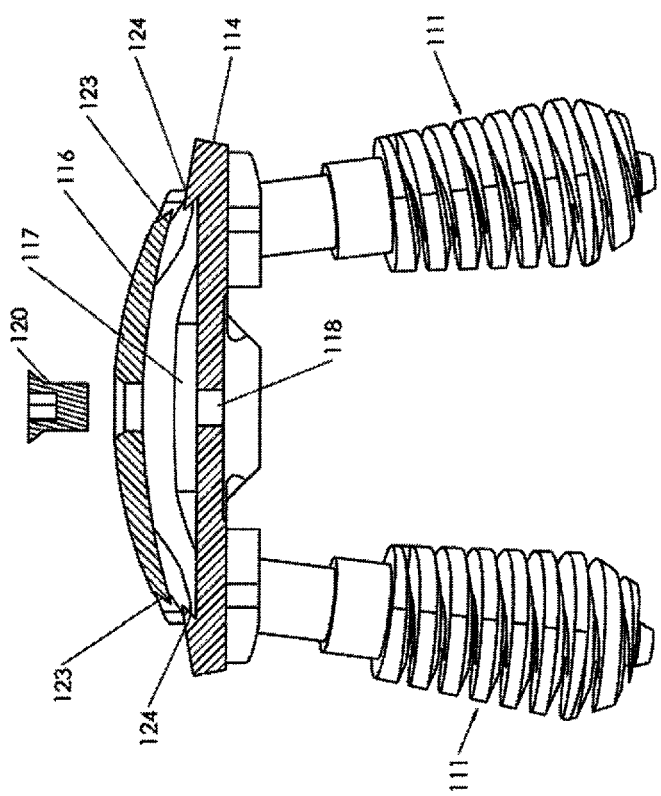
Figure 10A
Figure 10B

BONE FIXATION PLATE

CROSS REFERENCE TO RELATED APPLICATIONS

This application is a continuation-in-part of application Ser. No. 10/419,686, entitled "BONE FIXATION PLATE", filed Apr. 21, 2003, now U.S. Pat. No. 7,481,829, the entire contents of which is hereby expressly incorporated by reference.

FIELD OF THE INVENTION

This invention relates to the field of orthopedic surgery and, more particularly, to spinal fixation.

BACKGROUND OF THE INVENTION

The use of bone pins and plates for reducing fractures is well known in orthopedic medicine. The pins and plates extend across discontinuities in a bone to fix the broken ends in relation to each other to reduce pain and promote rapid healing without deformity. These devices are secured to the bone by bone screws or nails driven into the bone. More recently, pins, rods, plates and cages have been used to stabilize bone and joints that have deteriorated naturally or as a result of prior trauma. The bone plate of this invention is useful in all these situations.

The interface between the bone screws and the bone presents problems of stability and long term usage that have been addressed in different ways. One of the major problems is usually termed as back-out. This defines the condition in which the screws attaching the plate to the bone loosen over time, either relative to the bone or the plate or both. Severe back-out results in the bone screw working itself out of the bone and/or plate resulting in instability of the bone or joint. This situation results in increasing pain and danger from the instability, as well as, the movement of the screw. There may be several reasons for the back-out but anatomical stresses from body movements contribute greatly to the problem.

Prior art devices address the problem of back-out by use of secondary locking screws that hold the bone screws in the plate. The locking device engages the head of the bone screw and is tightened to fix the screw to the plate and, thus, the bone. Such devices are not particularly suited for deployment on the anterior aspect of the spine because of the close proximity of vital soft tissue organs which dictate a smooth, low profile, contoured surface.

Michelson, U.S. Pat. No. 6,454,771, discloses a bone plate for anterior cervical fixation. The plate has several holes for receiving bone screws. A locking screw mechanism is used to overlay the screw heads.

An expandable insert for placement between vertebrae is disclosed by Paes et al, U.S. Pat. No. 6,436,142. The device is in the nature of a lag screw and can expand with the insertion of an expansion screw.

U.S. Pat. No. 6,342,055 to Eisermann et al discloses a bone plate with bone screws having a snap-in retainer securing the heads to the plate.

Geisler, U.S. Pat. No. 6,231,610, discloses a bone plate with diverging bone screws and serrations on the plate to increase holding power.

U.S. Pat. No. 6,224,602 to Hayes discloses a bone plate with multiple bone screw holes which may be covered by a sliding locking plate. The bone plate has an undercut channel to hold the locking plate in contact with the screw heads. The locking plate is held to the plate by a locking screw once it is slid to the desired position.

Aust et al, U.S. Pat. No. 5,603,713, discloses an anterior lumbar plate attached by screws with various angular connections to the spine.

What is needed in the art is a less complicated system with multiple locking components for added security.

SUMMARY OF THE PRESENT INVENTION

It is an objective of this invention to provide a bone plate, suitable for anterior lumbar fixation, having countersunk screw holes, a low profile in cross section allowing the bone plate to be countersunk into the bone and a smooth distal surface to reduce the possibility of traumatizing adjacent soft tissue during use.

A further objective of the invention is to provide threaded tubular bone anchors embedded in bone guided by the screw holes in the plate. The bone anchors being screwed into the bone by external threads.

Another objective of the invention is to provide locking screws extending through the countersunk screw holes into the bone anchors with the leading ends of the screws expanding the ends of the bone anchors to fix the bone screws to the bone anchors and the anchors to the bone.

Yet another objective of the invention is to provide a bone plate with a locking cap which extends over the area of the countersunk screw holes. The locking cap fits into a large countersunk area of the bone plate covering the countersunk screw holes allowing easy and positive assembly and preventing relative lateral movement between the locking cap and the plate. The locking cap has an aperture and the plate has a receptacle which align when the cap is placed in the countersunk area. A cap screw is threaded into the aligned aperture and receptacle to connect the plate and the cap.

A still further objective of the invention is to provide a kit of several interchangeable components including plates, locking screws, anchors, caps and cap screws to permit the assembly of matching components to fit the anatomy of the patient.

Another objective of the invention is to provide a bone plate system with double headed locking screws and a cam on the bone plate to wedge into the double headed screws.

Another objective of the invention is to provide a bone plate system with a bone plate that can be used as a template for drilling holes into the bone prior to insertion of the bone anchors.

Another objective of the invention is to provide a bone anchor that is designed to be implanted by threadably passing the bone anchor through the bone plate for insertion into a pre drilled hole.

Another objective of the invention is to provide a bone anchor in the form of a deformable helical member.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 3 is a cross section of FIG. 2 along line 3-3;

FIG. 4 is a cross section of the bone plate counter sunk into the bone;

FIG. 5 is a bottom view of the bone plate with the cam rotated into the double headed screws;

FIGS. 8A through 8D are perspective views showing the bone plate, the bone anchor and the locking screw in various states of assembly.

FIG. 10A is a partially exploded side sectional view of the bone fixation plate with the locking cap unsecured to the bone plate.

FIG. 10B is a partially exploded perspective sectional view of the bone fixation plate with the locking cap unsecured to the bone plate.

DETAILED DESCRIPTION OF THE INVENTION

Figure 1:
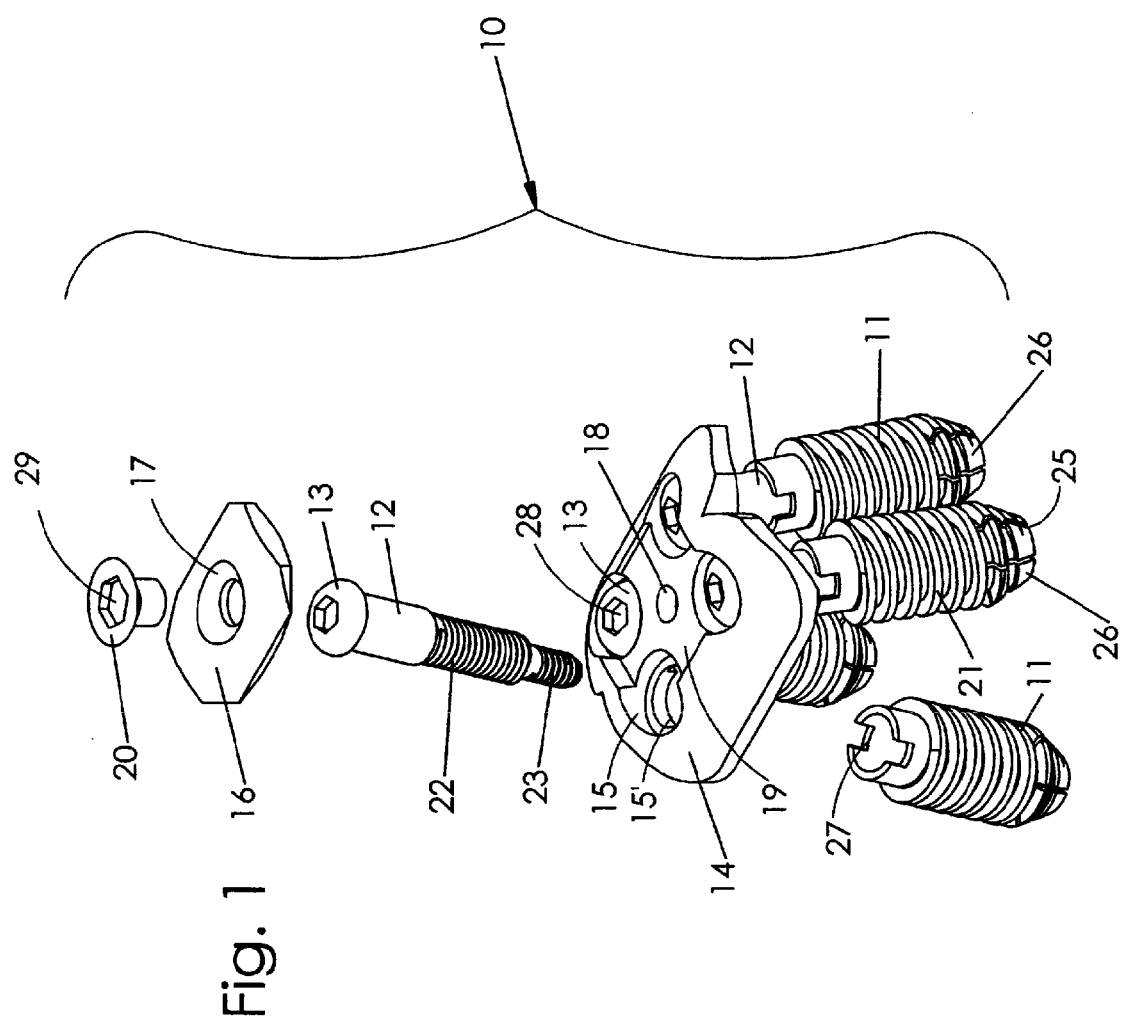
FIG. 1 is an exploded perspective view of the bone plate system of this invention.
Figure 2:
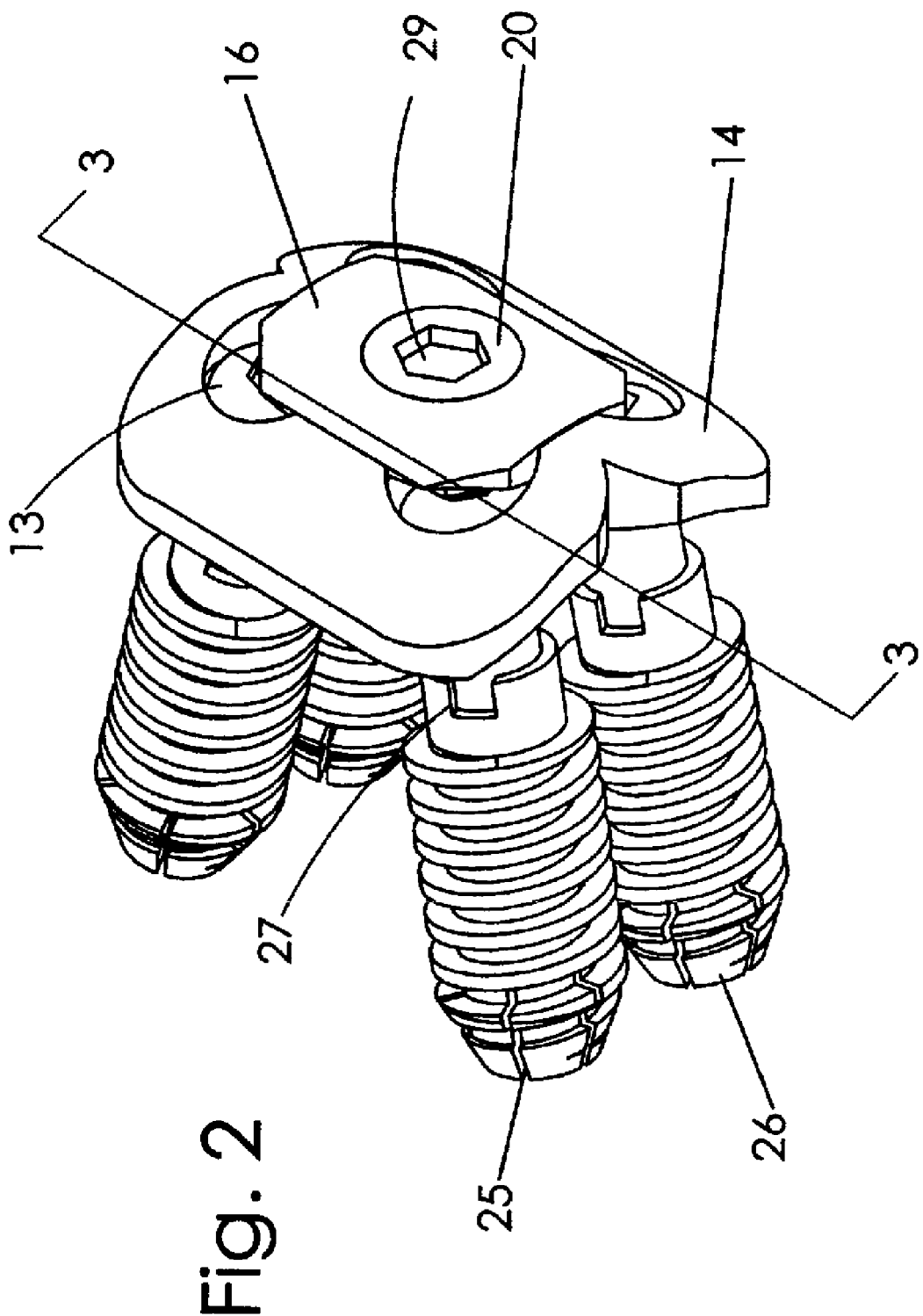
FIG. 2 is a perspective of assembled bone plate system of this invention.
Figure 2A:
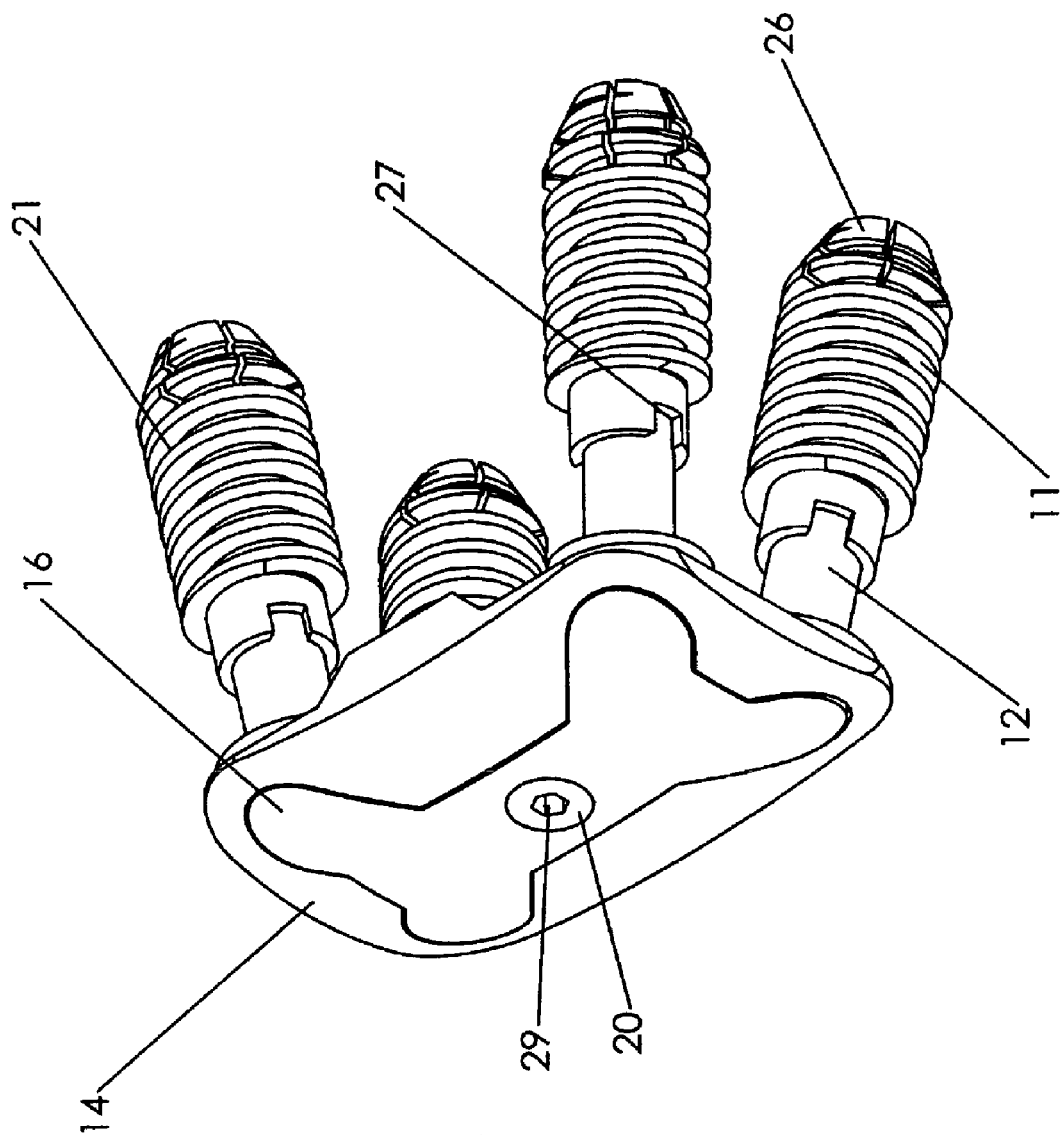
FIG. 2A is a perspective of another embodiment of FIG. 2.

The bone plate system 10 may be made from any materials having requisite strength and being suitable for use in the body. One complete bone plate system is shown in FIG. 1, FIG. 2 and FIG. 2A though it is understood that several different sizes of interchangeable components may be supplied together as a kit for mixing and matching components to size a system for a particular patient. A kit may have several different sized bone anchors 11 varying in diameter and length with complementary locking screws 12. The different sized locking screws may have the same sized heads 13 to be used in different sized bone plates 14 with screw holes 15' and countersunk depressions 15 of the same size. There may be several different sized locking caps 16, as shown in FIGS. 2 and 2A, to fit into the different complementary sized countersunk areas 19 of the plates while the aperture 17 and the threaded receptacle 18 are of the same size. The locking cap 16 is connected to the plate 14 by a cap screw 20. The kit merely refers to the dissembled components, shown in FIG. 1, that can be assembled to produce an integral whole which corresponds to the anatomical features of a particular patient.

The bone plate system 10 addresses the problem of backout by providing several locking features in the connection of the plate 14 with the bone. These locking features all resist the biomechanical loads placed on the implanted system and result in an aggregate resistance to movement of the components. The locking features are disposed over the length of the plate-bone connection such that the same biomechanical force may not act on all locks simultaneously.

The tubular bone anchors 11 are initially inserted into the bone through pilot holes drilled in the bone or by the use of guide wires. The plate 14 may be used as a guide to align the longitudinal axis of the bone anchors with the longitudinal axis of the countersunk screw holes 15' in the plate. The bone anchors 11 are driven into the bone with a tool (not shown) that engages the slots 27 for rotation of the anchor. The exterior screw threads 21 of the anchor draw the anchor into its seated position in the bone.

However, the screw threads 21 produce a mirror image of the toroidal ramp at the bone interface which is a path of least resistance in the opposite direction. The leading or proximal end of the anchor 11 has a number of radial slits 25 through the side wall dividing the proximal circumference into segments 26. Further, the leading end is tapered internally and externally toward a smaller end. This structure of the leading end of the bone anchors 11 creates a change in the bone-anchor interface by expanding, as the locking screws are inserted, to increase the resistance to reverse rotation.

Once the bone anchors 11 are in place, the locking screws 12 are extended through the screw holes 15' of the bone plate 14 with the threads 22 and 23 threadably engaging the interior threads 24 of the bone anchors. The locking screws are rotated by a tool (not shown) fitted into the receptacle 28. As shown, the locking screw 12 has a smooth unthreaded shank near the head 13. An intermediate length of the locking screw has threads 22 to engage the interior threads of the bone anchor. The leading end of the locking screw has a tapered portion with threads 23 to engage the threaded tapered leading end of the bone anchor. The threaded engagement of the locking screws with the leading ends of the anchors and the resultant expansion of the anchors creates a difference in the threading along the interior length of the anchor which resists rotation in the opposite direction. The leading end of the locking screws may be unthreaded and act as a wedge. The locking screw heads 13 are completely enclosed by the depressions 15 and compressively disposed against the bottoms of the depressions. Therefore, the anchor 11 is locked in place by a new bone-anchor interface and the locking screw and anchor are locked together by compression and threading changes. Of course, other combinations of locking screws and anchor configurations may be used, such as, a constant taper of each.

After the locking screws 12 have been seated in the bone anchors 11 and depressions 15, the locking cap 16 is placed in the complementary countersink 19 formed in the plate 14. The size and thickness of the locking cap and the size and depth of the countersunk area allow ease of assembly of these components and a resulting low profile with a smooth outer or distal surface. The vertebrae V is shaped to form a counter sunk area in which the plate is placed, as shown in FIG. 4. This is especially important in reducing the possibility of internal trauma to adjacent soft tissue, e.g., in the anterior lumbar spinal fixation.

The assembly of the locking plate 16 and the bone plate 14 automatically aligns the receptacle 16 and the aperture 17 for connection by the cap screw 20. The continuous side wall of the enlarged countersunk area and the periphery of the locking cap positively locate the components relative to each other. The cap screw 20 is tightened by a tool (not shown) that fits into receptacle 29. Once the locking cap is secured in place, the heads of the locking screws are prevented from retraction. Because the cap screw 20 is centrally located in the locking cap 16, any reverse rotation of the locking screws is opposed by a leveraging action between the locking cap and the cap screw. This action tends to jam the cap screw and locking cap tighter together.

Figure 6:
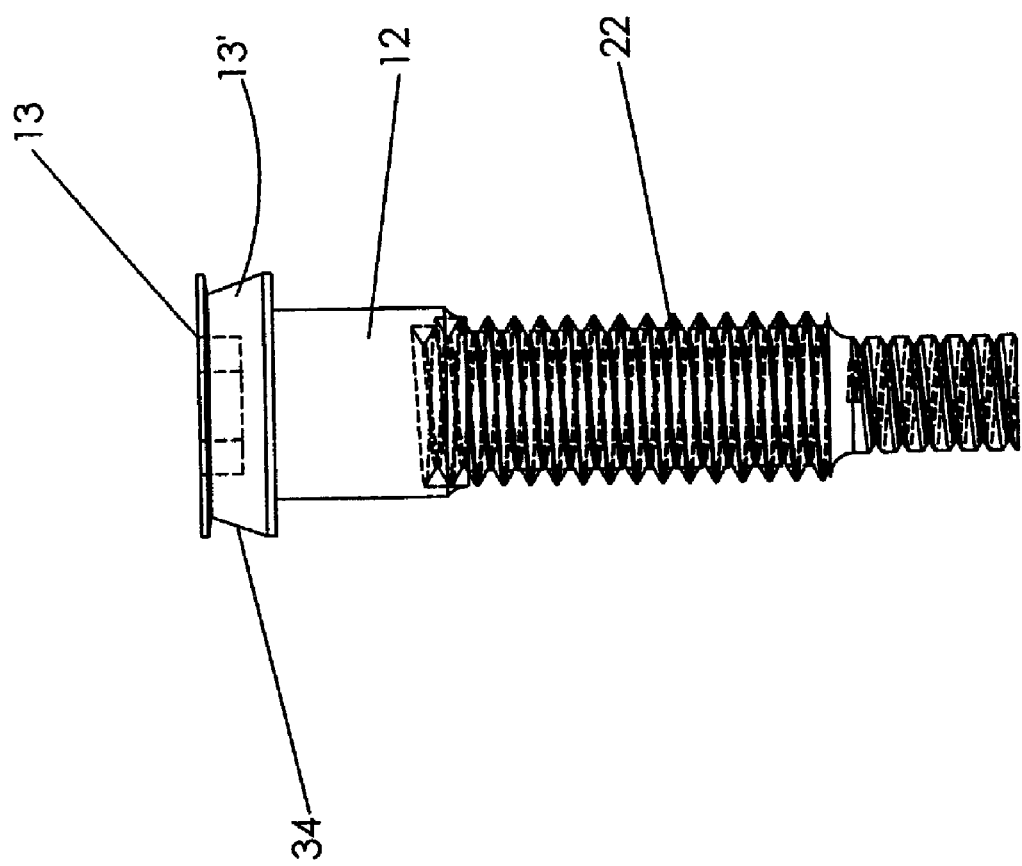
FIG. 6 is a perspective of a double headed locking screw.
Figure 7:
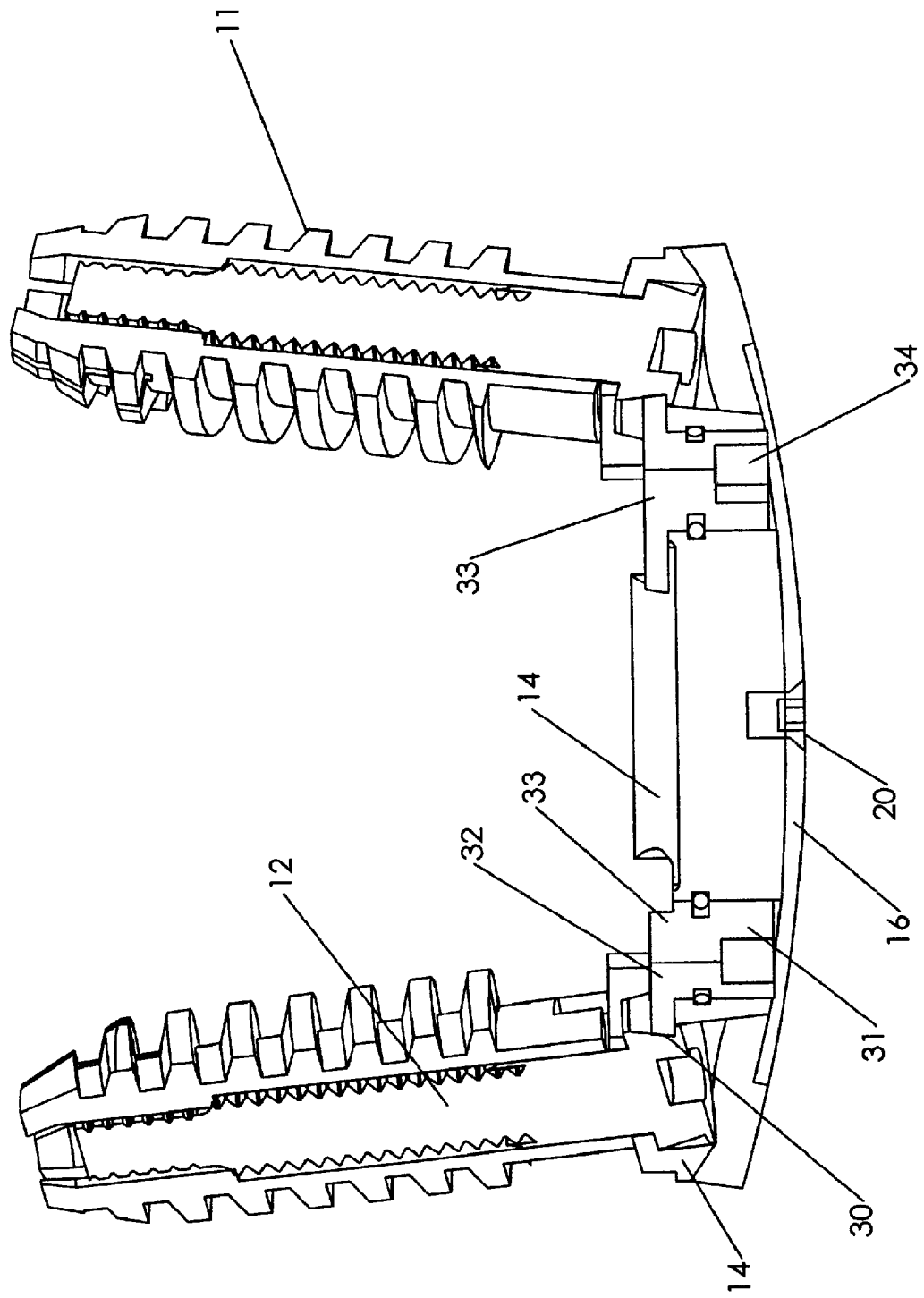
FIG. 7 is a cross section of a bone plate with a double headed screw in place.

As an alternative or additional attachment system is shown in FIGS. 5, 6, and 7. To further secure the locking screws 12 to the plate 14 requires a slit 30 in the side of each of the depressions 15. The slit in each adjacent depression faces the other. A cam 31 is rotatably mounted in the plate 14 between the adjacent depressions and has a flange formed with a blade portion 32 and a brake portion 33. The blade portion 32 will register with the slit 30 in one position and be free of the slit in another position. The brake portion 33 will engage the curved plate when the blade portion is registered with the slit 30 to create a friction stop. In this embodiment, the locking screws have a double headed configuration 13, 13' with a circumferential groove 34 between the two heads. When the locking screws are securely in place in the anchors 11 and plate 14, the grooves 34 will register with the slits 30. The cam 31 extends through the plate 14 into the countersunk portion 19 and is turned by a tool (not shown) to register the blade portion 32 with the slits 30 and the grooves 34. In this position, the brake portion 33 of the flange engages the curved surface of the plate 14. The locking cap 16 may then be applied, as described above. The cams may extend through the locking cap to be tightened along with the cap screw.

The implanted bone plate system results in a positive lock at the proximal ends of the bone anchors and locking screws and an additional lock at the distal end of the locking screws.

Figure 8C:
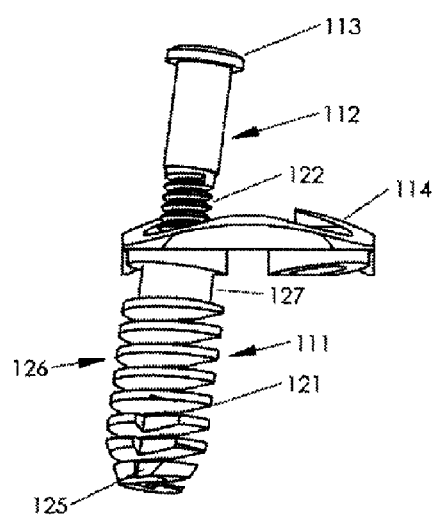
Figure 8D:
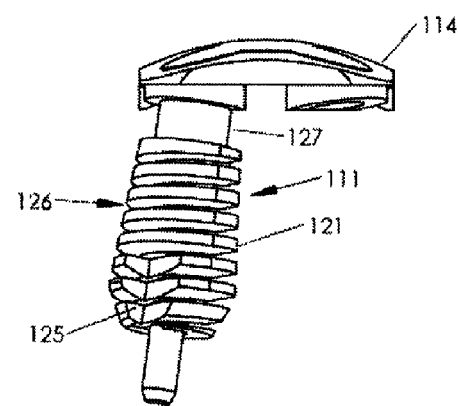
Figure 9B:
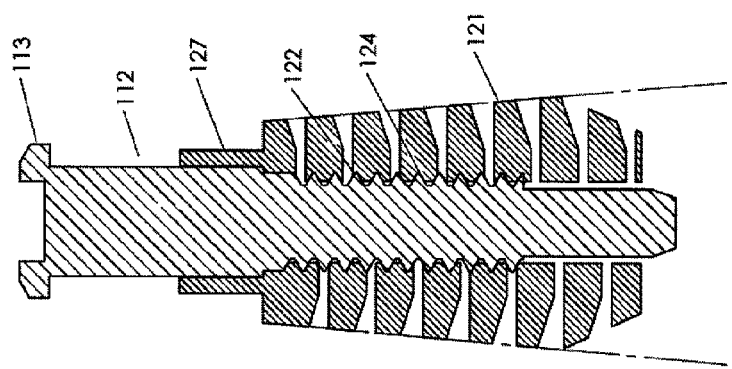
FIGS. 9A and 9B are cross section views of showing the relationship of the bone anchor and locking screw in various states of assembly.
Figure 9A:
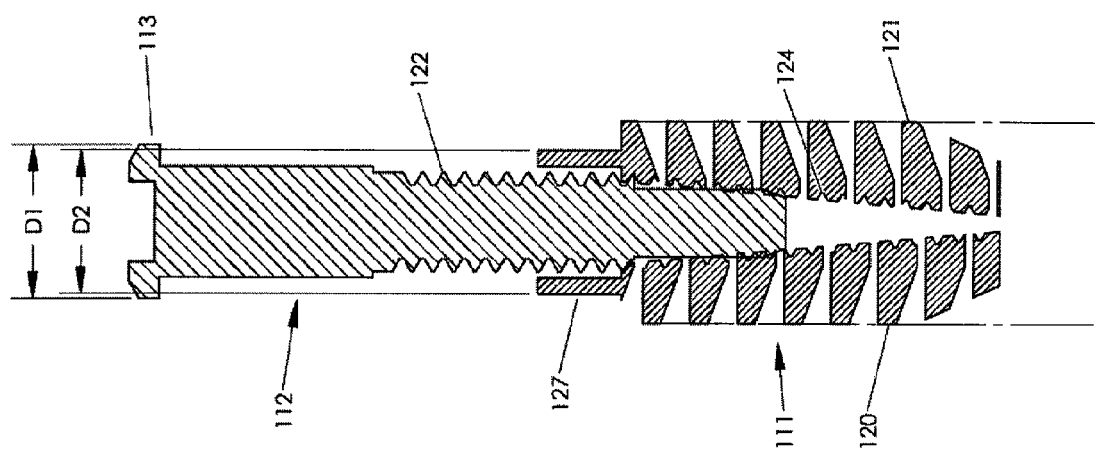

FIGS. 8A through 8D are perspective views showing an alternate embodiment of the bone fixation plate in various states of assembly. As shown in FIG. 8A each bone anchor 111 is threaded through the top surface of bone plate 114. In this embodiment the bone plate 114 can serve as a template for drilling pilot holes into the bone. Bone plate 114 includes screw holes 115, as shown in FIG. 10B. Each of the bone anchors 111 are rotatably threaded through the upper surface of bone plate 114 via screw holes 115. The upper end of each bone anchor 111 includes a collar portion 127. A tool (not shown) is capable of engaging collar portion 127 to impart rotation to bone anchor 111 and thread each bone anchor through the bone plate 114. As illustrated in FIGS. 9A and 9B, the threaded portion of anchor 111 is formed as a helical member 126 presenting an exterior threaded surface 121. Helical member 126 is configured as a deformable helical coil. Threaded surface 121 is threaded through screw hole 115. Collar 127 is smaller in diameter than screw hole 115. As initially positioned within the bone plate the outer diameter of the exterior threaded surface 121 has a constant outer diameter except for the first few lead-in threads which are somewhat reduced in diameter. The exterior threaded surface 121 of the helical member 126 is formed in profile as a buttress type thread. The interior circumferential surface of the helical member includes threads 124. As initially positioned, the diameter of threads 124 along the interior surface of helical member 126 decreases in size as it progresses from the collar end to the leading end. The leading end of each anchor 111 has one or more notches or flutes 125 on the exterior threaded surface 121. FIG. 8D illustrates the anchor member 111 threaded completely through bone plate 114.

Once the bone anchors 111 are fully situated within bone plate 114 a locking screw 112 will be threaded into each bone anchor 111. FIG. 8C shows a perspective of locking screw 112 partially inserted within bone anchor 111. Likewise, FIG. 9A shows a sectional view of locking screw 112 partially inserted within bone anchor 111. Each locking screw 112 includes a head portion 113, a smooth upper shank portion, an intermediate threaded portion 122, and a smooth lower shank portion. The locking screws are rotated by a tool (not shown) that engage head portion 113. Head portion 113 has a diameter D-1 greater than screw hole 115 in bone plate 114. The collar 127 has a diameter D-2 that is smaller than the diameter of the screw hole 115 in bone plate 114. The threaded portion 122 has a constant outer diameter. As shown in FIG. 9A, intermediate portion 122 engages threads 124 on the interior circumferential surface of helical member 126. As the locking screw 112 is threaded into the bone anchor 111 the smooth lower shank portion and the threaded 122 of locking screw 112 will increase the diameter of the interior circumferential surface of the helical member 126. Likewise, as the locking screw 112 is thread into the bone anchor 111 the outer circumferential surface of the helical member 126 is expanded. Except for the lead-in threads, the outer diameter of helical member 126 is greater at the leading end of the anchor 111 than at the collar end 127, as shown in FIG. 9B. Expansion of thread member 126 will cause thread surface 121 to penetrate bone tissue and create a strong bone-anchor interface.

Figure 11A:
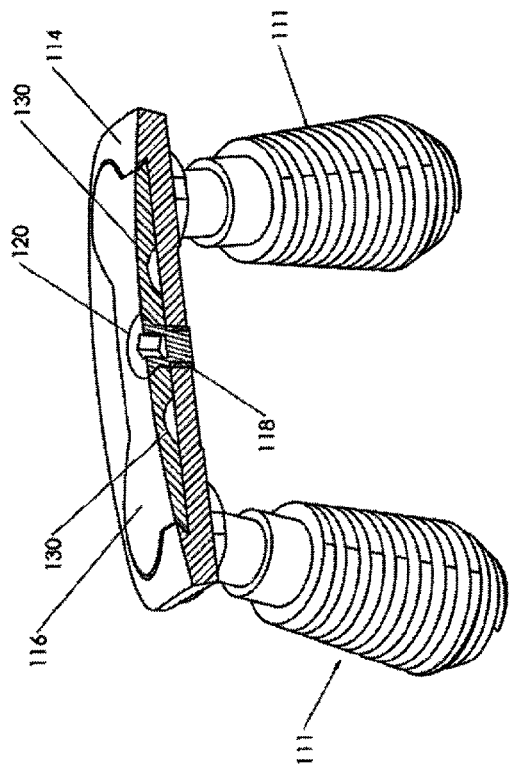
FIG. 11A is a side sectional view of the fully assembled bone fixation plate.
Figure 11B:
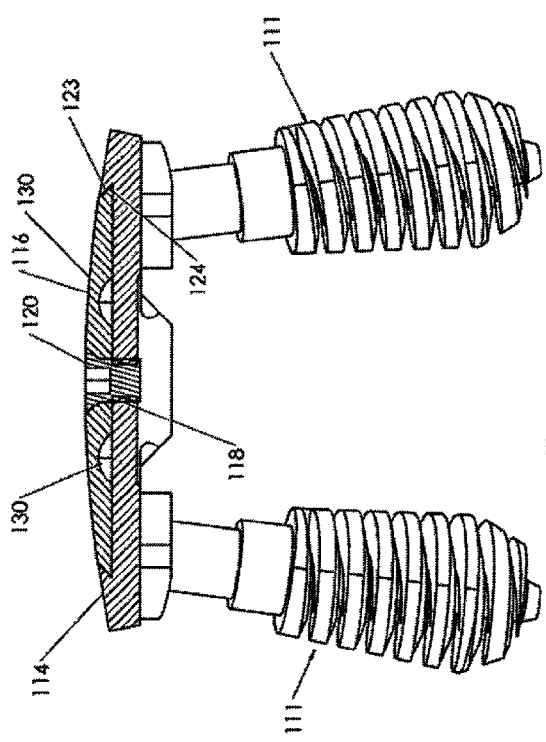
FIG. 11B is a perspective sectional view of the fully assembled bone fixation plate.

After the locking screws 112 have been seated within the bone anchors 111 a locking cap 116 is placed in a complimentary countersink area 119 in bone plate 114. The size and thickness of the locking cap 116 and the size and depth of the countersink area 119 allow for ease of assembly and result in a low profile having a smooth outer surface. Prior to installation the locking cap 116 is generally concave in overall configuration, as shown in FIGS. 10A and 10B. The cap 116 has an upper and lower surface and connecting side walls. The countersink area 119 has a shape that generally conforms to the shape of the locking cap 116 with upstanding side walls. The locking cap 116 includes a pair of chamfered side walls 123 at opposite ends that cooperate with complimentary recesses 124 in the side walls of countersunk recess area 119. The remaining side walls of the locking cap 116 and the walls of the countersink area 119 are substantially perpendicular to the upper and lower surfaces of the locking cap. Locking cap 116 includes an aperture 117. When the locking cap 116 is placed within the countersunk area 119, aperture 117 aligns with a threaded receptacle 118 located on bone plate 114. A locking cap screw 120 is placed within aperture 117 and threaded into threaded receptacle 118. As the cap screw 120 is threaded into its final position locking cap 116 is transformed from a generally concave configuration to a generally flat shape. In its fully assembled configuration, as shown in FIGS. 11A and 11B, chamfered edges 123 will be wedged underneath respective recesses 124 formed in the side walls of the countersunk area 119. Locking cap 116 may optionally includes slots, channels or grooves 130, as shown in FIGS. 11A and 11B, which will facilitate the flattening of locking cap 116 during assembly. The heads of the locking screws 112 are prevented from retraction once the locking cap is secured to the bone plate 114 by the cap screw 120. The bone plate, bone anchors, locking screws, locking cap and locking cap screw are made of titanium alloy or any suitable biocompatible material.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. A bone fixation kit for stabilizing skeletal bone across a discontinuity comprising:

a plate having a first end and a second end with an intermediate length to span a discontinuity and a width including at least one screw hole in each of said first end and said second end, said plate including a thickness with a first surface for contacting a bone and an opposite second surface, said plurality of screw holes extending through said thickness for accepting locking screws, said plurality of screw holes each having a first countersink defined by an enlarged depression in said second surface, each said depressions having a bottom wall between said first and said second surfaces, each said screw holes and each said depressions having a longitudinal axis;

a plurality of locking screws with each locking screw having external threads, each locking screw being adapted to penetrate each of said plurality of screw holes, said locking screws each having an enlarged head adapted to engage said bottom wall of each said depression; and an attachment system having a plurality of tubular bone anchors each having a helical member wherein each of the helical members is a deformable helical coil, each of said deformable helical coils includes a first end and a second end with interior threads and exterior threads, the turns of the deformable coil define the external threads while the internal surface of some of the turns of the deformable coil define a plurality of roots of the internal threads, wherein each of said tubular bone anchors has a uniform outer diameter that allows threading through said plate and positioned into a hole located in said skeletal bone, said interior threads of said helical members frictionally engaging the external threads on each of said locking screws, wherein said locking screws are inserted through said plate and are threadably engaged with said helical members for use in expanding the outer diameter of the external thread of said helical member to stabilize the bone across the discontinuity.

2. The bone fixation kit of claim 1 wherein the diameter of the internal threads of said helical members decreases in size from the first end of the helical member to the second end of the helical member when initially positioned in the bone plate prior to insertion of said locking screws.

3. The bone fixation kit of claim 1 wherein as the external threads of each of the helical members is increased in diameter the external threads are forced to penetrate bone tissue adjacent said hole to form a bone-anchor interface.

4. The bone fixation kit of claim 3 wherein the external threads of each of the helical members is formed in profile as a buttress type thread.

5. The bone fixation kit of claim 1 wherein said second surface of said plate conforms to a second countersink with a periphery, said second countersink having a depth, a locking cap adapted to be disposed in said second countersink and shaped to overlay a portion of each said first countersink of each of said screw holes, said locking cap having a first side to contact said plate and an opposite second side, a first threaded aperture in said intermediate length of said plate, a second threaded aperture in said locking cap, and a cap screw adapted to engage said second threaded aperture and said threaded first aperture to secure said locking cap in said plate.

6. A bone fixation kit of claim 5 wherein said second threaded aperture in said locking cap is countersunk in said distal side of said locking cap whereby said cap screw, said distal surface of said plate and said distal side of said locking cap form a smooth surface without projections whereby said locking screws are fixed in said bone anchors and prevented from backing-out of said plate by said locking cap.

7. A bone fixation kit of claim 6 wherein said the first and second sides of said locking cap prior to being secured to the plate are generally concave in overall configuration.

8. A bone fixation kit of claim 7 wherein said first and second sides of the locking cap are generally parallel to the surface of the second countersink when the locking cap is fully secured by said cap screw to the plate.

9. A bone fixation kit of claim 8 wherein the first side of said locking cap includes at least a pair of recess formations to facilitate the deformation of the locking cap from a generally concave configuration to a generally flat configuration.

10. A bone fixation kit of claim 5 wherein said locking cap includes an edge surface contiguous with said first side and said second side, said edge surface being generally perpendicular to said first and second sides except for at least two portions of said edge surface that are chamfered.

11. A bone fixation kit of claim 10 wherein said periphery of said second surface countersink includes at least two recesses that cooperate with said at least two portions of the edge surface that are chamfered when the locking cap is fully secured by said cap screw to the plate.

12. A bone fixation kit for stabilizing skeletal bone across a discontinuity comprising:

a plate having a first end and a second end with an intermediate length to span a discontinuity and a width including at least one screw hole in each of said first end and said second end, said plate including a thickness with a first surface for contacting a bone and an opposite second surface, said plurality of screw holes extending through said thickness for accepting locking screws, said plurality of screw holes each having a first countersink defined by an enlarged depression in said second surface, each said depressions having a bottom wall between said first and said second surfaces, each said screw holes and each said depressions having a longitudinal axis;

a plurality of locking screws with each locking screw having external threads, each locking screw being adapted to penetrate each of said plurality of screw holes, said locking screws each having an enlarged head adapted to engage said bottom wall of each said depression; and an attachment system having a plurality of tubular bone anchors each having a helical member including a first end and a second end with interior threads and exterior threads, the turns of the deformable coil define the external thread having a outer diameter while the internal surface of some of the turns of the deformable coil define a plurality of roots of the internal thread, wherein each of the helical members is a deformable helical coil said interior threads of said helical members frictionally engaging the external threads on each of said locking screws, wherein said locking screws are inserted through said plate and threadably engage said helical members for use in expanding the outer diameter of the external thread of said helical member to stabilize the bone across the discontinuity.

13. The bone fixation kit of claim 12 wherein said tubular bone anchors are threaded through said plate and positioned into a hole located in said skeletal bone.

14. The bone fixation kit of claim 13 wherein the diameter of the internal threads of said helical members decreases in size from the first end of the helical member to the second end of the helical member when initially positioned in the bone plate prior to insertion of said locking screws.

15. A bone fixation kit of claim 14 wherein said periphery of said second surface countersink includes at least two recesses that cooperate with said at least two portions of the edge surface that are chamfered when the locking cap is fully secured by said cap screw to the plate.

16. The bone fixation kit of claim 12 wherein as the external threads of each of the helical members is increased in diameter the external threads are forced to penetrate bone tissue adjacent said hole to form a bone-anchor interface.

17. The bone fixation kit of claim 16 wherein the external threads of each of the helical members is formed in profile as a buttress type thread.

18. The bone fixation kit of claim 12 wherein said second surface of said plate conforms to a second countersink with a periphery, said second countersink having a depth, a locking cap adapted to be disposed in said second countersink and shaped to overlay a portion of each said first countersink of each of said screw holes, said locking cap having a first side to contact said plate and an opposite second side, a first threaded aperture in said intermediate length of said plate, a second threaded aperture in said locking cap, and a cap screw adapted to engage said second threaded aperture and said threaded first aperture to secure said locking cap in said plate.

19. A bone fixation kit of claim 18 wherein said second threaded aperture in said locking cap is countersunk in said distal side of said locking cap whereby said cap screw, said distal surface of said plate and said distal side of said locking cap form a smooth surface without projections whereby said locking screws are fixed in said bone anchors and prevented from backing-out of said plate by said locking cap.

20. A bone fixation kit of claim 19 wherein said the first and second sides of said locking cap prior to being secured to the plate are generally concave in overall configuration.

21. A bone fixation kit of claim 20 wherein said first and second sides of the locking cap are generally parallel to the surface of the second countersink when the locking cap is fully secured by said cap screw to the plate.

22. A bone fixation kit of claim 21 wherein the first side of said locking cap includes at least a pair of recess formations to facilitate the deformation of the locking cap from a generally concave configuration to a generally flat configuration.

23. A bone fixation kit of claim 18 wherein said locking cap includes an edge surface contiguous with said first side and said second side, said edge surface being generally perpendicular to said first and second sides except for at least two portions of said edge surface that are chamfered.

24. A bone fixation device comprising;
a bone plate including at least one aperture,
at least one bone anchor including a helical member, said helical member being a deformable helical coil having a first end and a second end, said deformable helical coil having a threaded internal surface and a threaded outer surface presenting external threads, the turns of the deformable coil define the external thread while the internal surface of some of the turns of the deformable coil define a plurality of roots of the internal thread, said bone anchor having an outer diameter sized to be threadably received within said at least one aperture,
at least one locking screw having an externally threaded portion, said threaded portion having a diameter smaller than the diameter of said at least one aperture and a head portion that is larger in diameter than said at least one aperture, said threaded portion threadably received by the threaded internal surface of said at least one helical member expanding the outer diameter of the external thread of said helical member for use in stabilizing the bone across the discontinuity, and the head portion contacting a recessed portion located on a first surface of said bone plate,
a locking cap securely fastened to the first surface of the bone plate and covering said head portion of said at least one locking screw.

25. The bone fixation device of claim 24 including a plurality of apertures, a plurality of bone anchors and a plurality of locking screws.

* * * * *